US012558270B2

(12) United States Patent
Van Torre et al.

(10) Patent No.: US 12,558,270 B2
(45) Date of Patent: Feb. 24, 2026

(54) SENSING DIAPER CONTENT

(71) Applicants: UNIVERSITEIT GENT, Ghent (BE); IMEC VZW, Leuven (BE)

(72) Inventors: Patrick Van Torre, Lievegem (BE); Arno Moerman, Deinze (BE)

(73) Assignees: UNIVERSITEIT GENT, Ghent (BE); IMEC VZW, Leuven (BE)

( * ) Notice: Subject to any disclaimer, the term of this patent is extended or adjusted under 35 U.S.C. 154(b) by 321 days.

(21) Appl. No.: 18/268,839

(22) PCT Filed: Dec. 20, 2021

(86) PCT No.: PCT/EP2021/086842
§ 371 (c)(1),
(2) Date: Jun. 21, 2023

(87) PCT Pub. No.: WO2022/136295
PCT Pub. Date: Jun. 30, 2022

(65) Prior Publication Data
US 2024/0293266 A1 Sep. 5, 2024

(30) Foreign Application Priority Data
Dec. 21, 2020 (EP) ..................................... 20215973

(51) Int. Cl.
*A61F 13/42* (2006.01)
(52) U.S. Cl.
CPC ........ *A61F 13/42* (2013.01); *A61F 2013/424* (2013.01)
(58) Field of Classification Search
CPC .. A61F 13/42; A61F 2013/424; G01N 27/225
See application file for complete search history.

(56) References Cited

U.S. PATENT DOCUMENTS 5,760,694 A * 6/1998 Nissim .................... A61F 13/42
128/885
5,838,240 A 11/1998 Johnson
(Continued)

FOREIGN PATENT DOCUMENTS

WO 9742613 A2 11/1997
WO 2012160546 A1 11/2012
(Continued)

OTHER PUBLICATIONS

International Search Report from PCT Application No. PCT/EP2021/086842, Apr. 7, 2022.
(Continued)

*Primary Examiner* — Susan S Su
(74) *Attorney, Agent, or Firm* — Workman Nydegger

(57) ABSTRACT

A system for sensing diaper content includes a diaper, an outer coupling layer and a sensing circuitry. The diaper has a circuitry layer having inner input capacitor plates, tracks arranged to provide a resistive coupling between the inner capacitor plates dependent on the content, and inner output capacitor plates in galvanic contact with the respective inner input capacitor plates. The outer coupling layer contains outer input- and output capacitor plates arranged to form respective input- and output capacitors with the inner input- and output capacitor plates in the diaper when the outer coupling layer is provided onto the outside of the diaper. The sensing circuitry is arranged to apply an input signal onto the outer input capacitor plates, and to measure an output signal from the outer output capacitor plates resulting from the input signal and the resistive coupling thereby sensing the content.

13 Claims, 10 Drawing Sheets

(56)     References Cited

U.S. PATENT DOCUMENTS

| | | | | |
|---|---|---|---|---|
| 2013/0018340 A1 * | 1/2013 | Abraham | ................ | A61F 13/42 |
| | | | | 604/361 |
| 2022/0409443 A1 * | 12/2022 | Weber | ............... | A61F 13/49003 |

FOREIGN PATENT DOCUMENTS

| | | | |
|---|---|---|---|
| WO | 2016090492 A1 | 6/2016 |
| WO | 2019085776 A1 | 5/2019 |

OTHER PUBLICATIONS

Extended European Search Report from corresponding European Application No. 20215973.7, Jun. 2, 2021.

* cited by examiner

SENSING DIAPER CONTENT

TECHNICAL FIELD

Various example embodiments relate to the sensing of diaper content.

BACKGROUND

A diaper or nappy allows capturing excretion such as urine and faeces from the wearer. When the diaper is soiled it requires changing. In general, it is desirable to change the diaper when it is soiled to a certain extent in order to assure the wearer's comfort. In a lot of cases the wearer is not in the ability to signal that changing is required. A solution thereto is to provide in a sensing circuitry that monitors the diaper's content and allows signalling when changing is needed.

Such sensing can be done by providing a disposable passive or active circuitry within the diaper that measures the diaper content to some degree. The measurement is then brought to an outer reusable circuitry for further processing and signalling. Upon changing, the soiled diaper can be disposed and the outer circuitry can be reused and applied to a fresh diaper. The electronic circuitry can be printed on one of the inside layers of the diaper using conductive inks such as carbon- or silver based inks. The coupling with the outer circuitry can be done by a direct galvanic connection or by an indirect coupling, e.g. an inductive or radio frequency, RF, based coupling.

Current solutions still face several problems. While silver based conductive inks provide a good conductivity, they are expensive and pose an environmental risk upon disposal. The cheaper and cleaner carbon based inks on the other hand have a much lower conductivity making them difficult to use for inductive or RF coupling. Further, a direct galvanic connection requires punching through the diaper using probes or the provisioning of external clip-on contacts. This is however more cumbersome to apply and more prone to mistakes than indirect coupling.

WO9742613A2 discloses a disposable diaper. An outer sheath supports two conductive spaced-apart electrodes. The electrodes are in the form of conductive threads of wires. The electrodes terminate in widened pairs of adjacent fixedly spaced electrically-conductive pads on each end. Directly opposite the pad at each end are pouches. The pouches can receive a removable sensor having thin electrically-conductive rectangular planar members or surfaces. When a sensor sits in the pouch, the pair of members of the sensor, and the opposing pair of pads, form two adjacent capacitors. When a user wears and wets the diaper the liquid will electrolytically short-circuit the electrodes. As such, the electrodes operate as a conductive switch which is open, i.e. non-conductive, in a dry diaper and closed, i.e. conductive, in a wet diaper.

SUMMARY

The scope of protection sought for various embodiments of the invention is set out by the independent claims.

The embodiments and features described in this specification that do not fall within the scope of the independent claims, if any, are to be interpreted as examples useful for understanding various embodiments of the invention.

It is an object of the present disclosure to overcome the above identified problems.

This object is achieved, according to a first example aspect of the present disclosure, by a system for sensing diaper content comprising a diaper, an outer coupling layer and a sensing circuitry. The diaper comprises an inner circuitry layer having inner input capacitor plates, tracks arranged to provide a resistive coupling between the inner capacitor plates dependent on the diaper content, and inner output capacitor plates in galvanic contact with the respective inner input capacitor plates. The outer coupling layer comprises outer input- and output capacitor plates arranged to form respective input- and output capacitors with the inner input- and output capacitor plates in the diaper when the outer coupling layer is provided onto the outside of the diaper. The sensing circuitry is then further arranged to apply an input signal onto the outer input capacitor plates, and measure an output signal from the outer output capacitor plates resulting from the input signal and the resistive coupling thereby sensing the diaper content.

In other words, the inner circuitry layer is part of the diaper and provides the actual content sensing by means of the arranged tracks. The input signal is applied to these tracks and transformed to the output signal by the resistive coupling that is dependent on the diaper content, i.e., the attenuation of the input signal is dependent on the diaper content. Input and output signal are coupled between the inner circuitry layer and outer circuitry layer by a capacitive coupling. The coupling capacitors are formed by the inner plates within the diaper and by the outer plates of the outer coupling layer provided on the outside of the diaper wherein the diaper material between these layers serves as dielectric.

Further, as the input signal is applied to the input capacitors and the output signal is measured from the output capacitors, the resulting measurement is a 4-port transmission measurement describing how the input signal is transformed by the transmission path to the output signal. This transmission path is formed by the resistance of the inner capacitor plates, by the resistance of the tracks and by the resistive coupling between the tracks dependent on the diaper content.

It is an advantage that the sensing of diaper content by the inner circuitry layer is obtained by a passive circuitry as both the tracks and capacitor plates are passive electrical components. There is thus no need to provide active components within the diaper. It is a further advantage that there is no galvanic connection needed between the inner circuitry layer and outer coupling layer thereby avoiding the need for punching through the diaper or any other direct connection. Further, by the capacitive coupling and resistive sensing, the measurements do not require large currents. As a result, the inner circuitry layer does not require high conductance for the tracks and capacitor plates. Therefore, the tracks and inner capacitor plates may be made of materials having a low conductance, e.g. non-metal based conductive materials, while still achieving a good content sensing.

Advantageously, the inner circuitry layer is made of a low-cost printed conductive ink, for example a carbon-based conductive ink.

According to example embodiments, the diaper further comprises a moisture absorption layer and a comfort layer. The inner circuitry layer is then provided between the absorption layer and the comfort layer.

This way the circuitry layer doesn't hinder the wearer but still faces the absorption layer to obtain a good sensing of the content.

According to example embodiments the diaper comprises a barrier layer for keeping moisture within the diaper and the circuitry layer is provided onto the barrier layer. As such, the barrier layer serves as substrate for the circuitry layer.

According to example embodiments the outer coupling layer is attachable to and removable from the outside of the diaper, and is reusable when changing the diaper.

This way only the inner circuit layer is disposable with the diaper and the outer coupling layer is reusable. This allows producing the outer layer from better and more durable material thereby avoiding signal loss within the outer layer.

The outer layer may further comprise conductive tracks arranged to connect the outer capacitor plates with the sensing circuitry. This way, the sensing circuitry can connect to the outer layer in a more convenient location, e.g. on the front or back of the wearer.

According to example embodiments, the input signal comprises a differential input signal. The sensing circuitry is then arranged to apply the differential input signal between two outer input capacitor plates and to measure a differential output signal from two correspondingly connected outer output capacitor plates. In such case there are at least two input capacitors and two output capacitors formed by the inner and outer layers. By the use of differential signaling, external disturbances can be minimized resulting in a better content detection. The change in diaper content may then be detected by measuring a change in the differential output signal.

Further, the input signal may also comprise a common mode input signal. The sensing circuitry is then arranged to apply the common mode input signal to the two outer input capacitor plates, and to measure a common mode output signal from the two correspondingly connected outer output capacitor plates, and to compensate the measured diaper content for a change in electrical coupling between the input- and output capacitors based on the common mode output signal.

According to example embodiments a first inner input capacitor plate of the inner input capacitor plates and a first inner output capacitor plate of the inner output capacitor plates are provided at distal ends of a first track of the tracks and wherein a second inner input capacitor plate of the inner input capacitor plates and a second inner output capacitor plate of the inner output capacitor plates is provided at distal ends of a second track of the tracks thereby defining a detection zone for sensing the diaper content between the first and second track.

This topology creates a relatively long distance between the input and output plates because the track is located in between them. The resistive coupling is then provided between the different tracks along this long distance, i.e. the tracks are arranged from inputs to outputs in a series configuration. By this topology very small quantities in diaper content can be detected.

According to example embodiments a first inner input capacitor plate of the inner input capacitor plates and a first inner output capacitor plate of the inner output capacitor plates is provided at a same distal end of a first track of the tracks and wherein a second inner input capacitor plate of the inner input capacitor plates and a second inner output capacitor plate of the inner output capacitor plates is provided at a same distal end of a second track of the tracks thereby defining a detection zone for sensing the diaper content between the first and second track.

This topology creates a short distance between the input and output plates in comparison with the track itself thereby arranging the tracks in a shunt configuration. By this topology differences in diaper content can be detected when having high moisture levels.

According to a further embodiment, the diaper comprises a third inner input capacitor plate and a third inner output capacitor plate connected to a third track and defining another detection zone between the third and first track wherein the first input and output capacitor plate serve as a common node.

This way, two pairs of differential input- and output signals can be applied while only needing six capacitor plates.

According to a second example aspect, a diaper according to the system of the first example aspect is disclosed.

BRIEF DESCRIPTION OF THE DRAWINGS

Some example embodiments will now be described with reference to the accompanying drawings.

DETAILED DESCRIPTION OF EMBODIMENT(S)

Figure 1A:
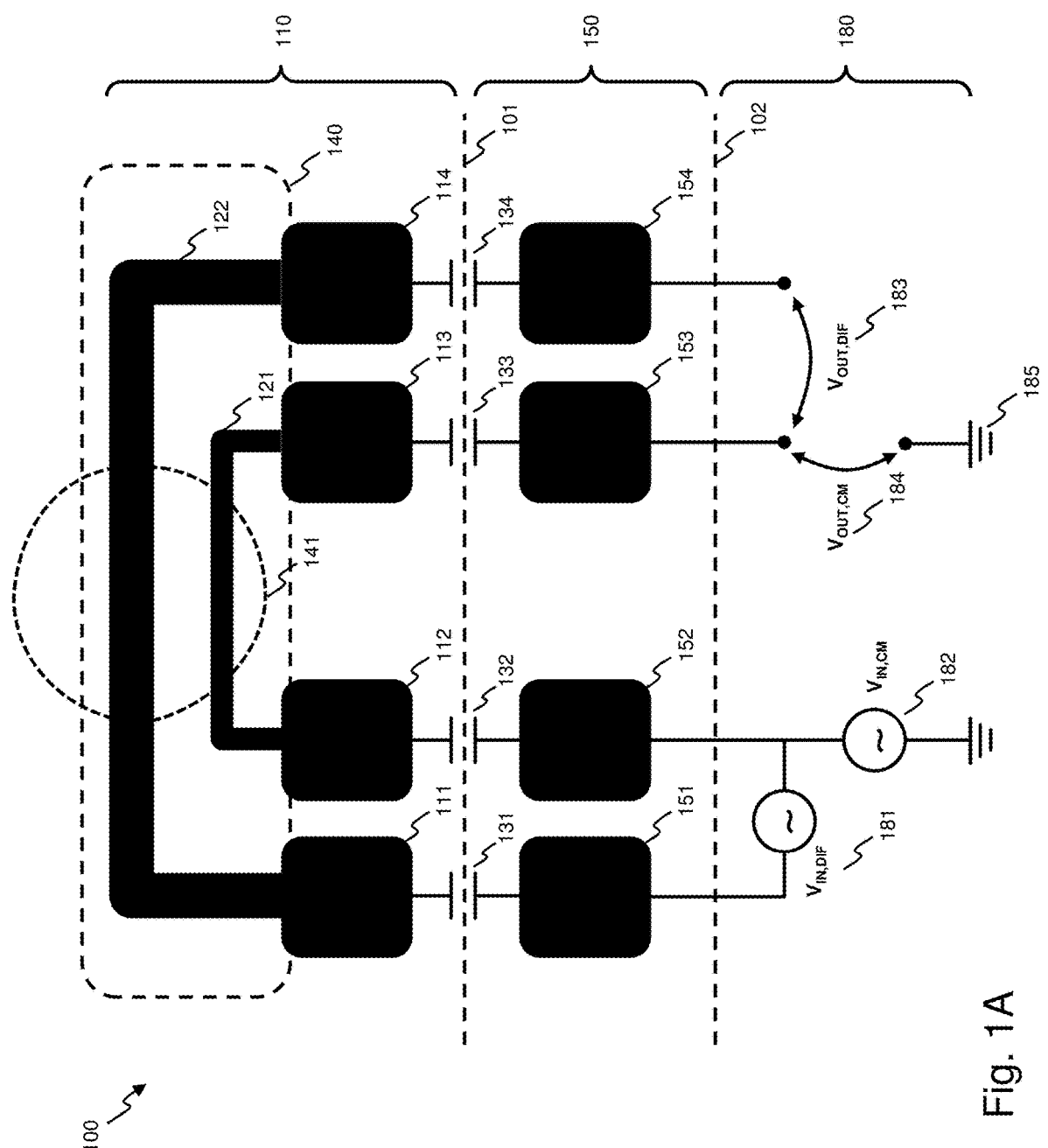
FIG. 1A shows an example embodiment of a system for detecting diaper content in a series configuration.
Figure 1B:
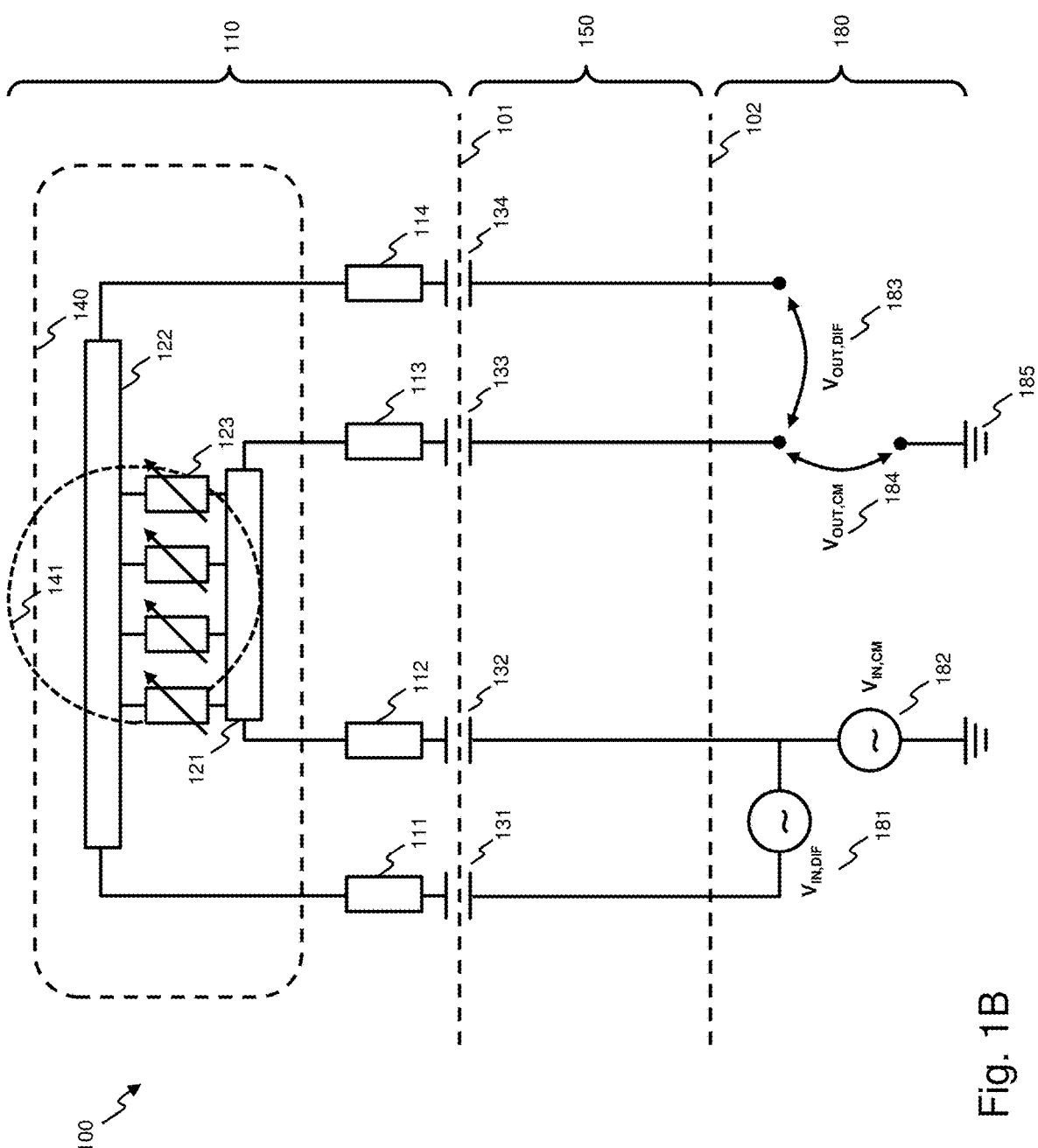
FIG. 1B shows a circuit representation of the system shown in FIG. 1A.

FIGS. 1A and 1B illustrate a system 100 for sensing diaper content 141 according to an example embodiment. System 100 comprises a diaper 110, an outer coupling layer 150 and a sensing circuitry 180. The diaper 110 is provided with an inner circuitry layer that is provided within the diaper 110. The inner circuitry layer comprises input capacitor plates 111, 112, conductive tracks 121, 122 and output capacitor plates 113, 114. A first input capacitor plate 111 is connected by a first conductive track 122 with a first output capacitor plate 114 thereby galvanically connecting capacitor plate 111 with capacitor plate 114. Similarly, a second input capacitor plate 112 is connected by a second conductive track 121 with a second output capacitor plate 113. Input capacitor plates 111, 112 are thereby in galvanic contact with the respective output capacitor plates 114, 113. The conductive tracks 121, 122 define a detection area or zone 140 within the diaper 110. When there is diaper content within this detection zone 140, as illustrated by the dashed circle 141, then the resistance between the first and second track 121, 122 will decrease due to the moisture in the diaper content 141. While FIG. 1A illustrates the inner circuitry layer by a layout of its components, FIG. 1B illustrates the inner circuitry layer as an electrical circuitry wherein the tracks 121, 122 and inner capacitor plates 111, 112, 113, 114 are represented by resistors and the resistive coupling caused by the moisture is represented by the variable resistors 123. As such, a transmission path is formed which will transform input signals 181, 182 to the output signals 183, 184. This transmission path is then formed from input to output by the serial resistor formed by resistors 111, 122, and 114, by the serial resistor formed by resistors 112, 121, and 113, and by the variable parallel resistor formed by the variable resistor 123.

System 100 further comprises an outer coupling layer 150 further comprising input coupling capacitor plates 151, 152 and output coupling capacitor plates 153, 154. The coupling capacitor plates 151-154 are arranged on the coupling layer 150 such that they form respective capacitors 131-134 with the respective capacitor plates 111-114 as provided in the diaper 110. As a result, input capacitor plates 151, 152 allow receiving an input electrical signal 181, 182 and coupling the electrical signal into the inner circuitry layer. Similarly, output capacitor plates 153, 154 allow coupling out an electrical signal from the inner circuitry layer as output electrical signals 183, 184.

System 100 further comprises a sensing circuitry 180. Sensing circuitry 180 is arranged to apply a differential input signal 181 between input coupling capacitor plates 151 and 152, i.e. a signal characterized by the voltage difference that is applied between the plates 151 and 152. Sensing circuitry 180 may further be arranged to apply a common mode signal 182 to both input coupling capacitor plates 151, 152, i.e. a signal characterized by the voltage difference between a common ground node 185 and one of the input coupling plates 151, 152. Input signals 181, 182 will be coupled into the diaper 110 by capacitors 131, 132 and appear as voltages on the input capacitor plates 111, 112. Dependent on the moisture content within detection zone 140, the applied input signals 181, 182 will cause electrical output voltages on the output capacitor plates 113-114. By coupling capacitors 133-134, the output voltages are coupled out of the diaper onto the output coupling capacitor plates 153-154. Sensing circuitry 180 then measures the differential output signal 183 as the electrical voltage difference between the plates 153 and 154. Sensing circuitry 180 may further measure the common mode output signal 184 as the electrical voltage difference between a common ground node 185 and one of the output coupling plates 153-154.

Figure 2B:
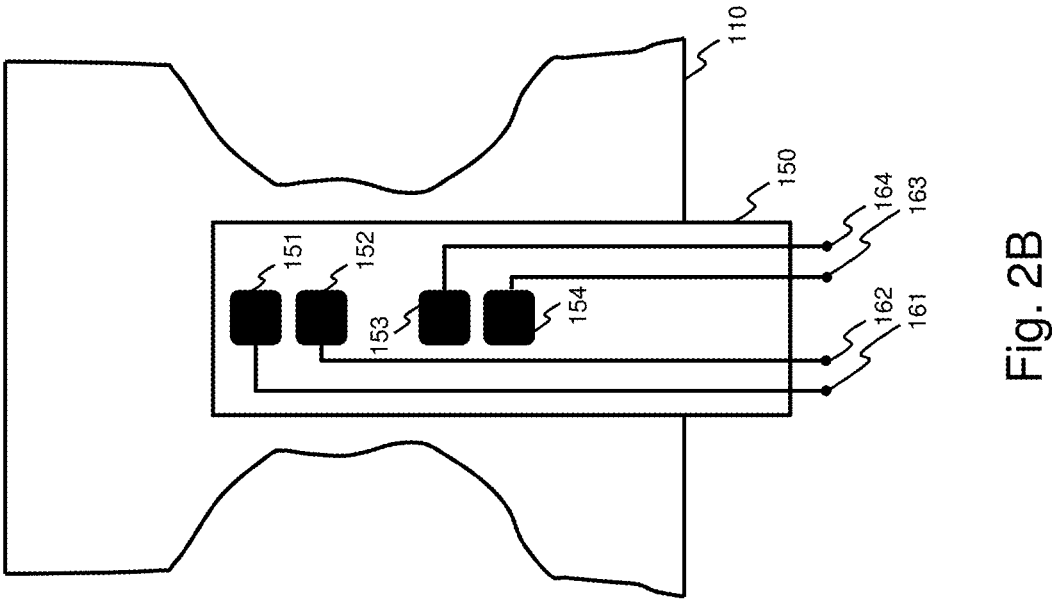
FIG. 2B shows the diaper of FIG. 2A from the outside and an outer layer attachable to the diaper for coupling to the inner circuitry layer.
Figure 2A:
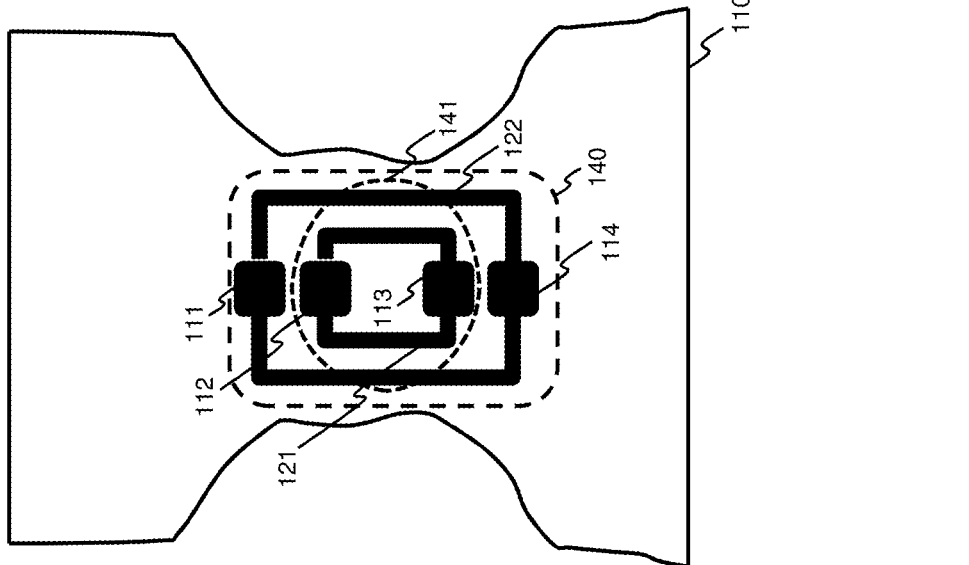
FIG. 2A shows an example embodiment of a diaper having an inner circuitry layer for detecting diaper content in a series configuration.

FIGS. 2A and 2B show a top view of a same diaper 110 according to an example embodiment. FIG. 2A illustrates an example arrangement of the capacitor plates 111-114 and tracks 121-122 as the inner circuitry layer within the diaper. The tracks are provided in the middle section of the diaper 110 thereby defining the detection zone 140 in a central zone of the diaper 110. In order to have a large detection zone 140 with a single pair of input and output capacitor plates, two instances of both the first track 121 and second track 122 are provided. The circuitry within the diaper 110 is not necessarily visible from the inside or outside as will be described further below.

FIG. 2B shows the coupling layer 150 on the outside of the same diaper 110 when arranged on the outside of the diaper 110. Outer coupling capacitor plates 151-154 are positioned and aligned on top of inner capacitor plates 111-114 in order to form respective capacitors 131-134. Coupling layer 150 may further comprise conductive tracks connecting the capacitor plates 151-154 to contacts 161-164 for connecting the coupling layer 150 to sensing circuitry 180. Coupling layer 150 may be removable from diaper 110. This way, when changing diaper 110, the coupling layer 150 can be removed and reused on a fresh diaper. To this purpose, the coupling layer and/or diaper may be provided with removable fastening means such as a touch fastener or a pressure sensitive adhesive.

Figure 3A:
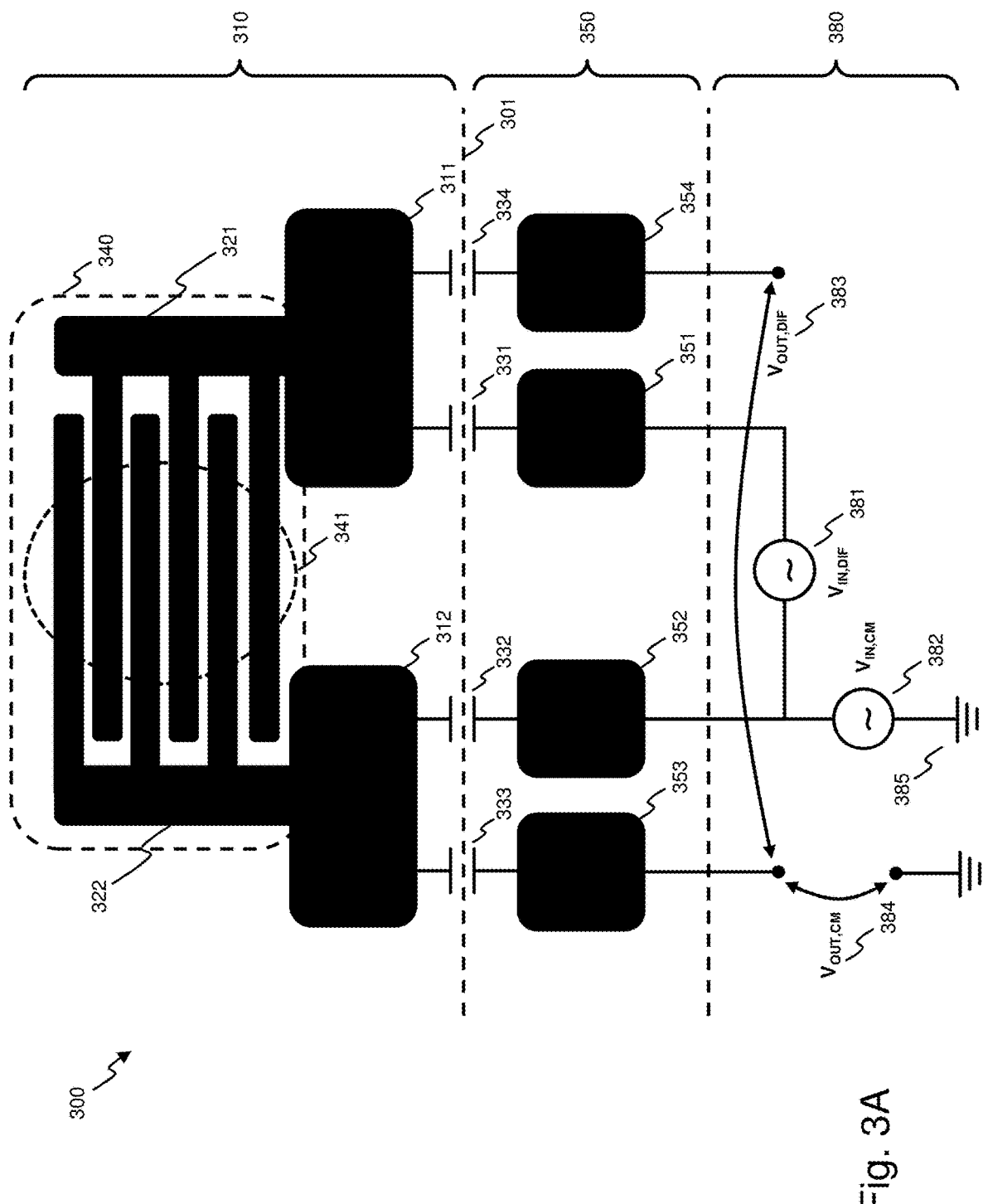
FIG. 3A shows an example embodiment of a system for detecting diaper content in a shunt configuration.
Figure 3B:
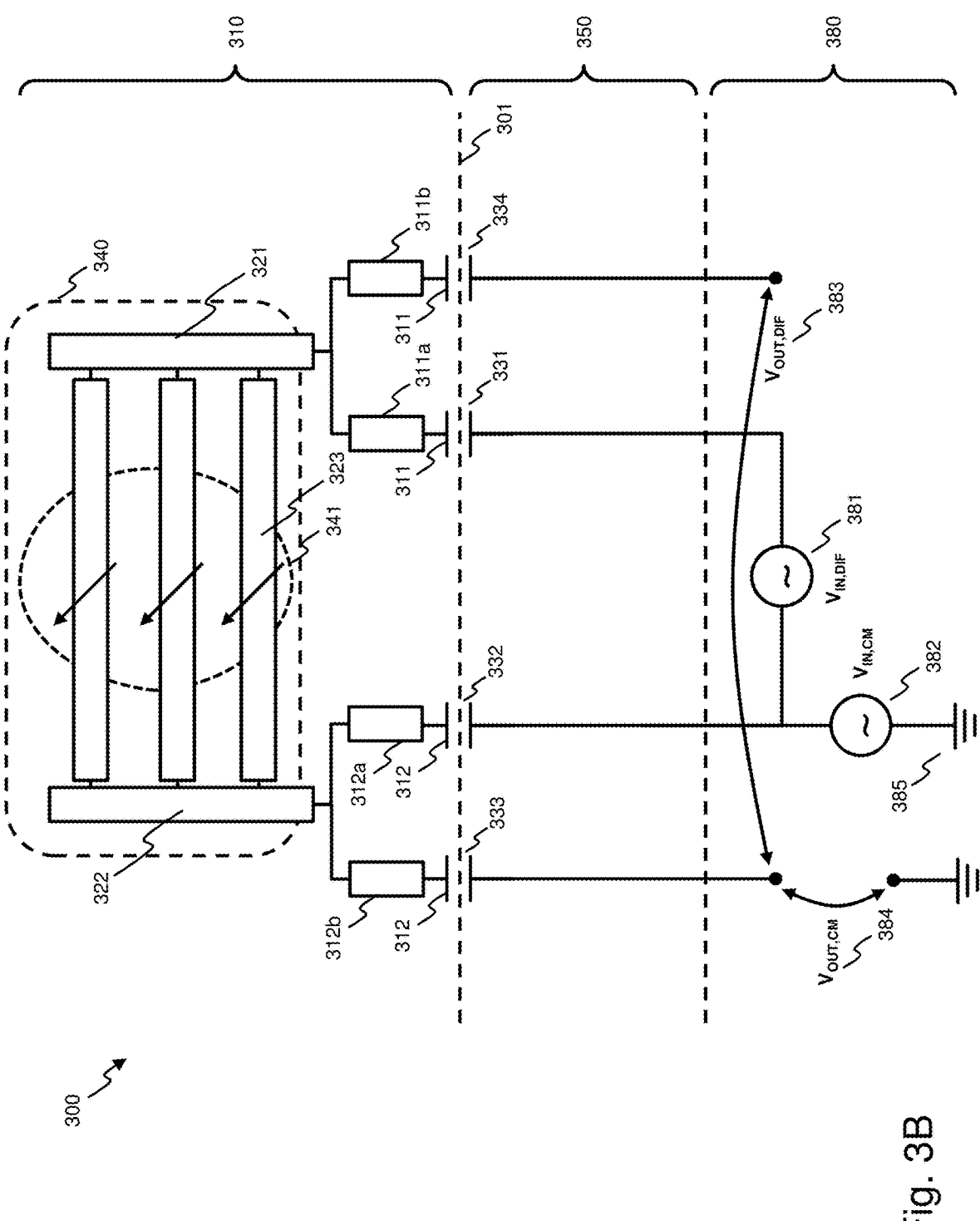
FIG. 3B shows a circuit representation of the system shown in FIG. 3A.

FIGS. 3A and 3B illustrate a system 300 for sensing diaper content 341 according to another example embodiment. System 300 comprises a diaper 310, an outer coupling layer 350 and a sensing circuitry 380. The diaper 310 is provided with an inner circuitry layer that is provided within the diaper 310. The inner circuitry layer comprises input capacitor plates 311, 312, conductive tracks 321, 322 and output capacitor plates 311, 312. The respective input and output capacitor plates are connected to each other thereby forming joined input and output capacitor plates 311, 312.

A first conductive track 322 extends from input- and output capacitor plate 312 and a second conductive track 321 extends from input- and output capacitor plate 311. First and second track 321, 322 may both branch out into a plurality of sub-tracks. The sub-tracts are then arranged alternatingly next to one another thereby defining a detection zone 340. When there is diaper content within this detection zone 340, as illustrated by the dashed circle 341, then the resistance between the branches of the first and second track 321, 322 will decrease due to the moisture in the diaper content 341. While FIG. 3A illustrates the inner circuitry layer by a layout of its components, FIG. 3B illustrates the inner circuitry layer as an electrical circuitry wherein the tracks are represented by resistors 321, 322, capacitor plate 312 is represented by resistors 312$a$ and 312$b$, capacitor plate 311 is represented by resistors 311$a$ and 311$b$, and the resistive coupling caused by the moisture is represented by the variable resistors 323. As such, a transmission path is formed which will transform input signals 381, 382 to the output signals 383, 384. This transmission path is then formed from input to output by input serial resistors 311$a$, 312$a$, by the variable parallel resistor formed by the series of resistors 321, 323 and 322, and by the output serial resistors 311$b$ and 312$b$.

System 300 further comprises an outer coupling layer 350 further comprising input coupling capacitor plates 351, 352 and output coupling capacitor plates 353, 354. The coupling capacitor plates 351-354 are arranged on the coupling layer 350 such that they form respective capacitors 331-334 with the capacitor plates 311, 312 as provided in the diaper 310. More particular, input coupling plate 351 forms capacitor 331 with capacitor plate 311 and input coupling plate 352 forms capacitor 332 with capacitor plate 312. Similarly, output coupling plate 353 forms capacitor 333 with capacitor plate 312 and output coupling plate 354 forms capacitor 334 with capacitor plate 311. As a result, input capacitor plates 351, 352 allow receiving an input electrical signal 381, 382 and allow coupling the input electrical signal into the circuitry within the diaper 310. Similarly, output capacitor plates 353, 354 allow coupling out an electrical signal from the circuitry within the diaper 310 as output electrical signals 383, 384.

System 300 further comprises a sensing circuitry 380. Sensing circuitry 380 is arranged similarly to sensing circuitry 180, i.e. to apply a differential input signal 381 between input coupling capacitor plates 351 and 352, i.e. a signal characterized by the voltage difference between the plates 351 and 352. Sensing circuitry 380 may further be arranged to apply a common mode signal 382 to both input coupling capacitor plates 351, 352, i.e. a signal characterized by the voltage difference between a common ground node 385 and one of the input coupling plates 351, 352. Input signals 381, 382 will be coupled into the diaper by capacitors 331, 332 and appear as voltages on the input capacitor plates 311, 312. Dependent on the moisture content within detection zone 340 input signals 381, 382 will result in electrical output voltages on the capacitor plates 311, 312. By coupling capacitors 333-334, the output voltages are coupled out of the diaper onto the output coupling capacitor plates 353-354. Sensing circuitry 380 then measures the differential output signal 383 as the electrical voltage difference between the plates 353 and 354. Sensing circuitry 380 may further measure the common mode output signal 384 as the electrical voltage difference between a common ground node 385 and one of the output coupling plates 353-354.

Figure 4B:
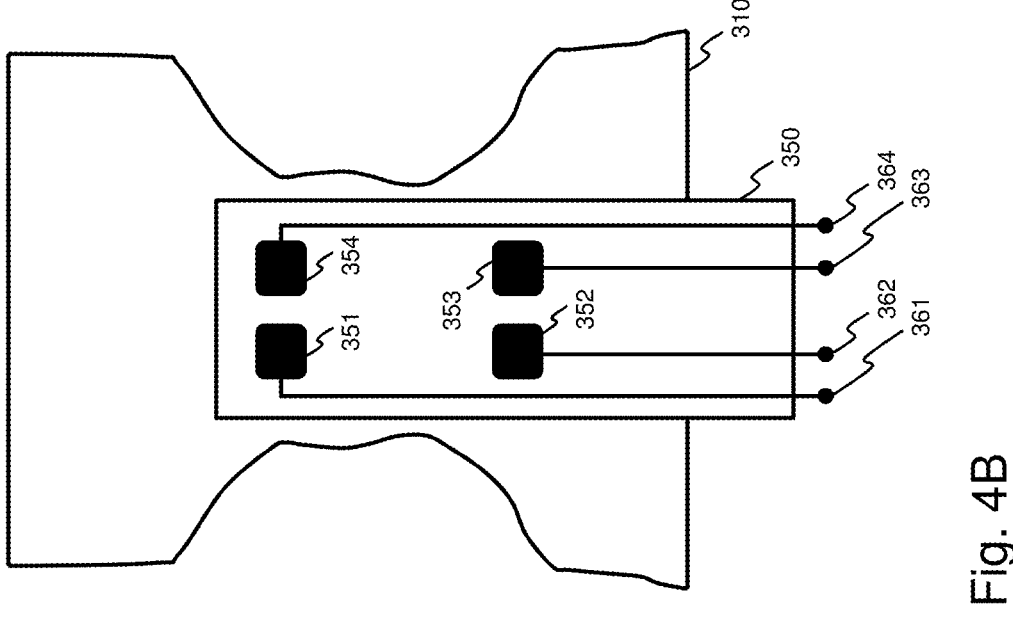
FIG. 4B shows the diaper of FIG. 4A from the outside and an outer layer attachable to the diaper for coupling to the inner circuitry layer.
Figure 4A:
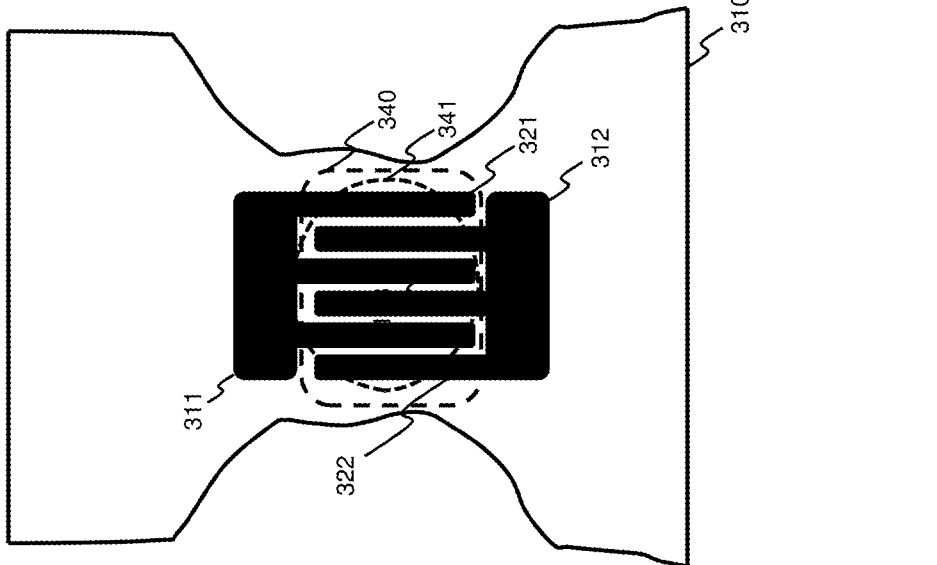
FIG. 4A shows an example embodiment of a diaper having an inner circuitry layer for detecting diaper content in a shunt configuration.

FIGS. 4A and 4B show a top view of a same diaper 310 according to an example embodiment. FIG. 4A illustrates an example arrangement of the capacitor plates 311, 312 and tracks 321-322 within the diaper. The tracks are provided in the middle section of the diaper 310 thereby defining the detection zone 340 in a central zone of the diaper 310. In order to have a large detection zone 340 for one pair of input and output capacitor plates, a plurality of sub-tracks extend from the capacitor plates 311, 312. The circuitry within diaper 310 is not necessarily visible from the inside or outside as will be described further below.

FIG. 4B shows the coupling layer 350 on the outside of the same diaper 310 when arranged on the outside of the diaper. Coupling capacitor plates 351 and 354 are positioned on top of inner capacitor plate 311 and coupling capacitor plates 352 and 353 are positioned on top of inner capacitor plate 312. Coupling layer 350 may further comprise conductive tracks connecting the capacitor plates 351-354 to contacts 361-364 for connecting the coupling layer 350 to sensing circuitry 380. Coupling layer 350 may be removable from diaper 310. This way, when changing diaper 310, the coupling layer 350 can be removed and reused on a fresh diaper. To this purpose, the coupling layer and/or diaper may be provided with removable fastening means such as a touch fastener or a pressure sensitive adhesive.

Figure 5:
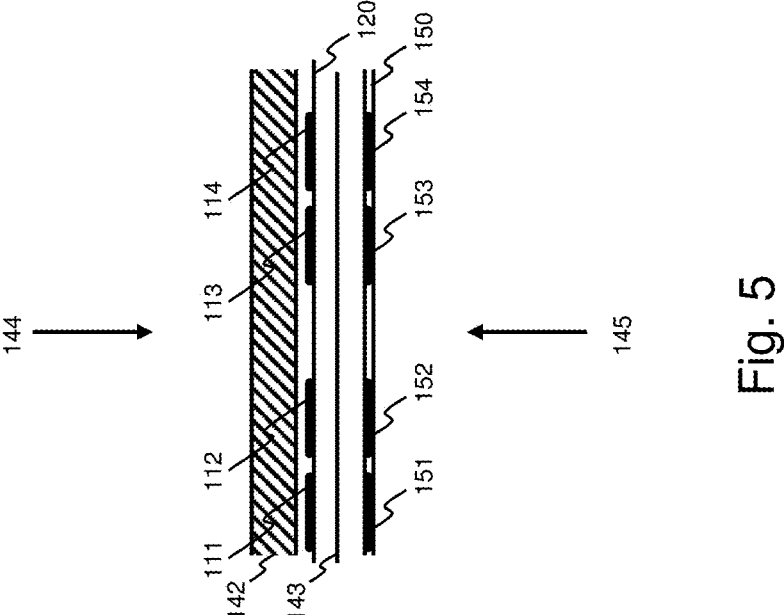
FIG. 5 shows a cross section of a diaper and outer layer according to an example embodiment.

FIG. 5 illustrates a cross-section of the diaper 110 and coupling layer 150 according to an example embodiment. The cross-section may also apply in a similar way to the above described diaper 310 and coupling layer 350. The diaper 110 comprises a first moisture absorbing layer 142 provided to the inside portion 144 of the diaper, i.e. the side 144 facing the wearer's skin when worn. Absorbing layer 142 may contain any moisture absorbing and retaining material such as superabsorbent polymers. Diaper 110 further comprises a circuitry layer 120 that contains the inner capacitor plates 111-114 and tracks 121, 122. Circuitry layer 120 may have a combined function as a moisture barrier layer wherein the circuitry components are provided onto the inner side 144 of such a moisture barrier layer. The moisture barrier layer serves as a moisture barrier in case wet content would leak through the absorbing layer 142. Diaper 110 may further comprise a comfort layer 143 serving as the outer layer of the diaper. Comfort layer 143 is selected to provide a comfortable feel and touch, e.g. by incorporating a soft woven material. When worn, coupling layer 150 is arranged on the outside 145 of the diaper 110 onto the comfort layer 143 in a way that the capacitor plates 151-154 align with the capacitor plates 111-114 within the diaper 110 as already described above. The gap and material between the capacitor plates then provide a galvanic isolation between the plates and serve as dielectric for the so-obtained capacitors.

Figure 6:
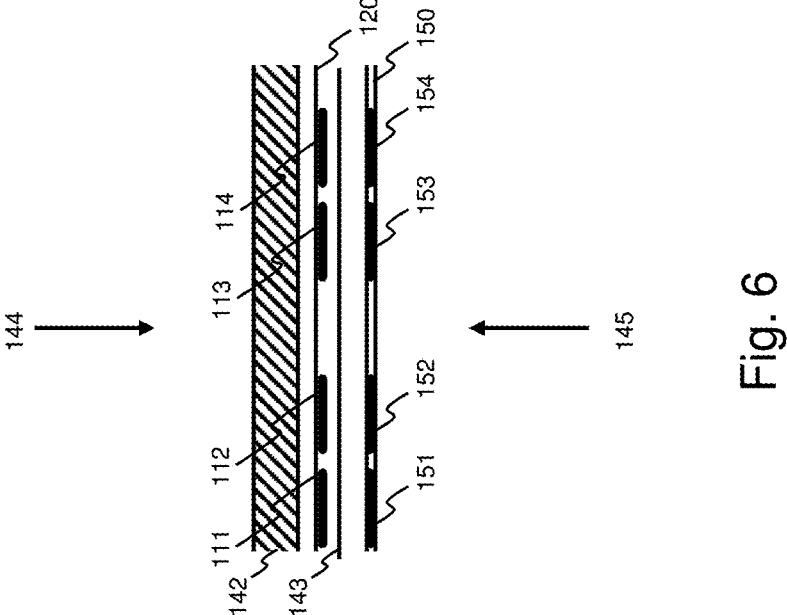
FIG. 6 shows a cross section of a diaper and outer layer according to an example embodiment.

FIG. 6 illustrates a cross-section of the diaper 110 and coupling layer 150 according to another example embodiment. Only the differences with the embodiment of FIG. 5 will be described. In FIG. 6, the diaper 110 also comprises a circuitry layer 120. The conductive components, i.e. capacitor plates 111-114 and tracks 121-122, are now provided on the outside 145 the circuitry layer 120, e.g. on the outside of a moisture barrier layer 120. Again, this cross-section may also apply in a similar way to the above-described diaper 310 and coupling layer 350.

According to example embodiments the described capacitor plates and tracks within the inner circuitry layer are deposited onto a substrate layer such as the moisture barrier layer. Preferably, the depositing is performed by printing the circuitry layout onto the substrate layer using conductive inks, i.e. an ink that conducts electricity when printed onto the substrate. The conductivity of the ink may be based on the presence of conductive metal or carbon particles in the ink. Advantageously, a low cost ink that can be disposed in an environmentally friendly way is used, for example a carbon based ink. Such ink then contains any form of conductive carbon such as graphite, carbon nanotubes or amorphous carbon. In general, carbon based ink has a relatively low conductivity in comparison with metal based inks such as silver based conductive inks. The conductivity of carbon based ink is generally in the order of 2000 to 100 S/m (siemens per metre). A metal based conductive ink generally has a conductivity well above 20000 S/m with silver based inks having a conductivity in the order of $1 \cdot 10^7$ S/m. As the input and output signals are coupled capacitively into and out of the circuitry layer, much lower currents can be used than when using magnetic or radio-frequency based signal coupling. Because of the capacitive coupling, the resistance of the tracks 121, 122, 321, 322 will have less effect on the measured output signal. Therefore, low conductive inks can be used for the capacitor plates and tracks while keeping a satisfactory tracking and/or detecting of the diaper content.

According to example embodiments, the capacitor plates and tracks of the coupling layer 150, 350 are metal based, e.g. copper or silver based. These components may for example be provided onto a flexible substrate that follows the form of the diaper. The substrate may for example be made of flexible plastic such as polyimide, polyether ether ketone (PEEK) or transparent conductive polyester film.

Both inner circuitry layers according to FIGS. 1A and 3A provide a resistive coupling between the input and output capacitor plates that is dependent of the diaper content within the detection zone. FIG. 1A provides a series arrangement of the tracks with the connected input- and output capacitor plates. This series arrangement is most useful for detecting small amounts of diaper contents, i.e. when the diaper is still relatively dry. FIG. 3A provides a shunt arrangement of the tracks with the connected input- and output capacitor plates. This parallel arrangement is most useful for detecting changes in the diaper content when the diaper is already relatively wet.

Figure 7:
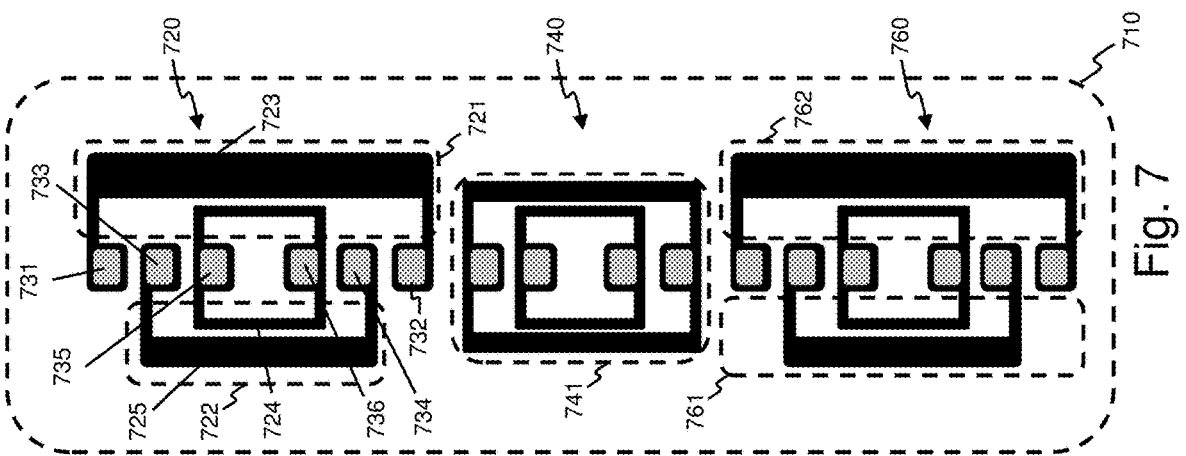
FIG. 7 shows a layout of a circuitry provided in a diaper for detecting diaper content according to an example embodiment.

FIG. 7 illustrates a diaper 710 comprising different inner circuitry layers 720, 740 and 760 for sensing diaper content according to an example embodiment. Top circuitry 720 comprises a first common track 724 containing two sub tracks connected at opposing distal ends to a first input capacitor plate 735 and a first output capacitor plate 736. Top circuitry 720 further comprises a second track 723 connected at opposing distal ends to a second input capacitor plate 731 and a second output capacitor plate 732. Top circuitry 720 further comprises a third track 725 connected at opposing distal ends to a third input capacitor plate 733 and a third output capacitor plate 734. First and second tracks 724, 723 then define a first detection zone 721 for detecting diaper content when applying an input signal to input capacitor plates 731, 735 and measuring the output signal at output capacitor plates 736, 732 according to the current disclosure. Similarly, first and third tracks 724, 725 then define a second detection zone 722 for detecting diaper content when applying an input signal to input capacitor plates 733, 735 and measuring the output signal at output capacitor plates 736, 734 according to the current disclosure. The two detection zones 721 and 722 are thus using the same capacitor plates 735, 736 as common nodes thereby saving an additional input and output capacitor plate than when using two times the layout of the circuitry according to FIG. 1A. The same layout is used for circuitry 760 thereby defining detection zones 761 and 762 at an opposing side of the diaper 710. As the middle section of a diaper is typically narrower (not shown), a smaller circuitry 740 defining a single detection zone 741 is provided in that location. The tracks of circuitry 740 are divided into two subtracks thereby defining the detection zone 741 symmetrically around the capacitor plates. Preferably, the width of the tracks 723-725 is selected such that the resulting conductance of the tracks is the same as for track 724. This way, the contribution of the tracks to unbalance in case of a differential mode output signal is cancelled out.

Figure 8:
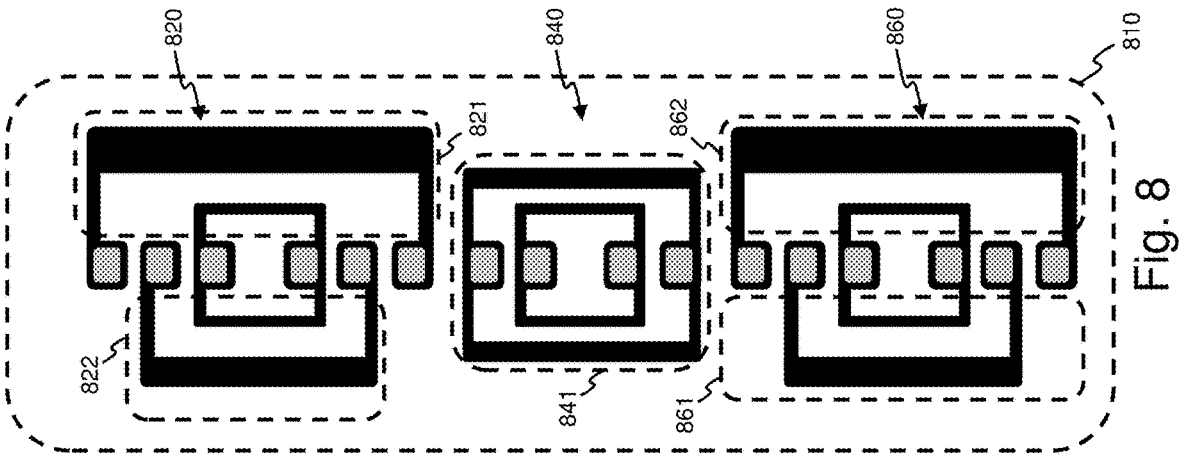
FIG. 8 shows a layout of a circuitry provided in a diaper for detecting diaper content according to an example embodiment.

FIG. 8 illustrates a diaper 810 comprising different circuitries 820, 840 and 860 for sensing diaper content according to an example embodiment. The layout of the circuitries is the same as those of diaper 710 except that the distance between the different tracks is larger thereby obtaining larger detection zones 821, 822, 841, 861, 862.

Figure 10:
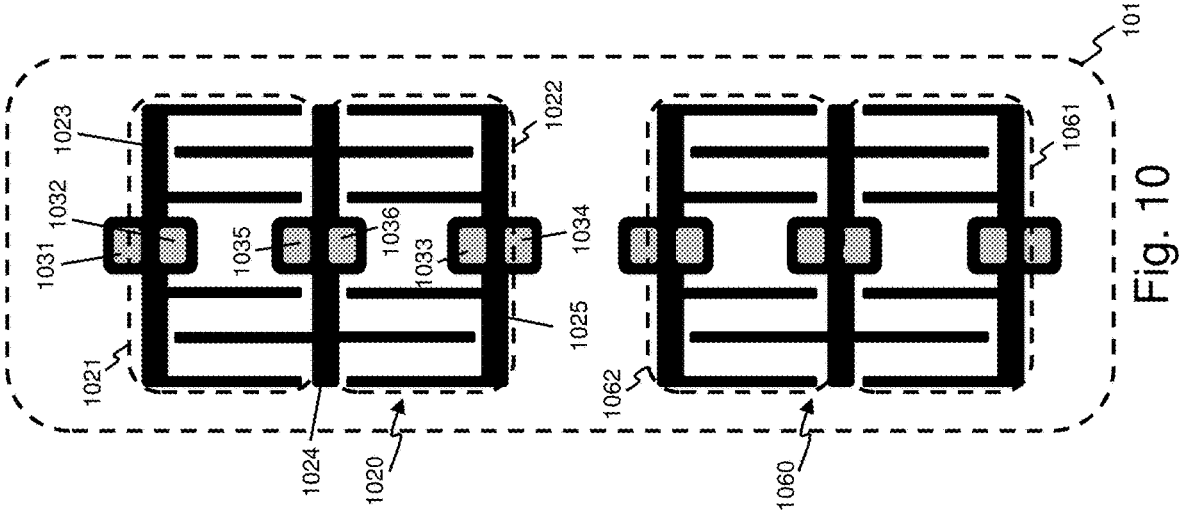
FIG. 10 shows a layout of a circuitry provided in a diaper for detecting diaper content according to an example embodiment.

FIG. 10 illustrates a diaper 1010 comprising different circuitries 1020 and 1060 for sensing diaper content according to an example embodiment. Top circuitry 1020 comprises a first common track 1024 extending into different sub tracks towards both a top and bottom portion of the diaper 1010. In the middle of track 1024, a first input capacitor plate 1035 and a first output capacitor plate 1036 are provided. Top circuitry 1020 further comprises a second track 1023 from which different sub tracks extend adjacent to the sub tracks of track 1024. A second input capacitor plate 1031 and a second output capacitor plate 1032 are further connected to the middle of track 1023. Top circuitry 1020 further comprises a third track 1025 from which different sub tracks extend adjacent to the sub tracks of track 1024. A third input capacitor plate 1033 and a third output capacitor plate 1034 are further connected to the middle of track 1025. First and second tracks 1024, 1023 then define a first detection zone 1021 for detecting diaper content when applying an input signal to input capacitor plates 1031, 1035 and measuring the output signal as output capacitor plates 1032, 1036 as described with reference to FIGS. 3A and 3B. Similarly, first and third tracks 1024, 1025 then define a second detection zone 1022 for detecting diaper content when applying an input signal to input capacitor plates 1033, 1035 and measuring the output signal as output capacitor plates 1034,1036 as described with reference to FIGS. 3A and 3B. The two detection zones 1021 and 1022 are thus using the same capacitor plates 1035, 1036 as common nodes thereby saving an additional input and output capacitor plate than when using two times the layout of the circuitry according to FIG. 3A. The same layout is used for circuitry 1060 thereby defining detection zones 1061 and 1062 at an opposing side of the diaper 1010. This layout may be used for detecting high moisture levels.

Figure 9:
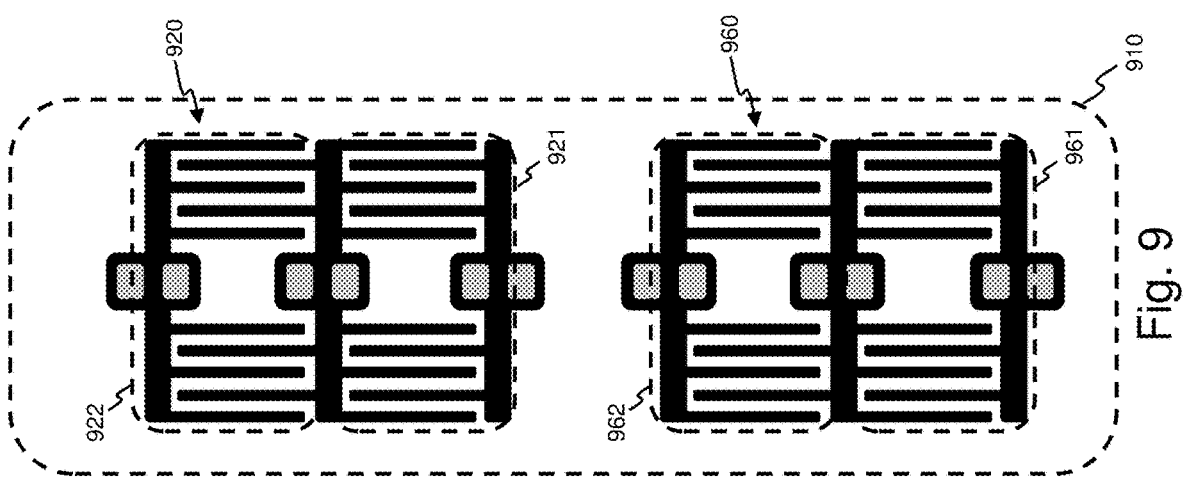
FIG. 9 shows a layout of a circuitry provided in a diaper for detecting diaper content according to an example embodiment.

FIG. 9 illustrates a diaper 910 comprising different circuitries 920 and 960 for sensing diaper content according to an example embodiment. The layout of the circuitries is the same as those of diaper 1010 except that there are more sub tracks provided, benefiting the detection of intermediate moisture levels.

According to example embodiments the sensing circuitry 180, 380 is arranged to generate the differential and common mode signals. As input signal, a single frequency signal may be used. The frequency range of the signal may be selected from a range from 1 kHz to 100 MHz, preferably from 100 kHz to 10 MHz. Good diaper content detection was obtained with frequencies around 1 MHz. Using a single frequency input signal results in a low cost for both the input and output signal processing. The input signal may also sweep over a certain frequency range, e.g. from 100 KHz to 10 MHz. This results in more accurate results as different frequencies will provide better measurements depending on the diaper content. The sensing circuitry is further arranged to measure the output signals 183, 184 and 383, 384 and to generate therefrom a measure of the diaper's content. In general, the diaper's content will be inversely proportional with the signal amplitude of the output signal. Thereto, a DC signal proportional to the measured signal amplitude may be generated from both the measured differential and common mode signal. These DC signals may then be sampled for further digital processing. In particular, the differential and common mode signal can be combined into a single measure of the diaper content. The common mode signal then characterizes the amount or level of coupling between the coupling layer and the actual detection zone. The differential signal characterizes the actual diaper content when there is a certain constant signal coupling. However, when the coupling changes, the differential output signal will change for the same diaper content. This type of coupling disturbance may be mitigated by considering the ratio between the differential output signal and common mode output signal as a characterization of the diaper content. In such case, a change in coupling between coupling layer and diaper circuitry will be compensated for. As a result, the detection is more accurate and false positives or negatives are avoided.

Figure 11:
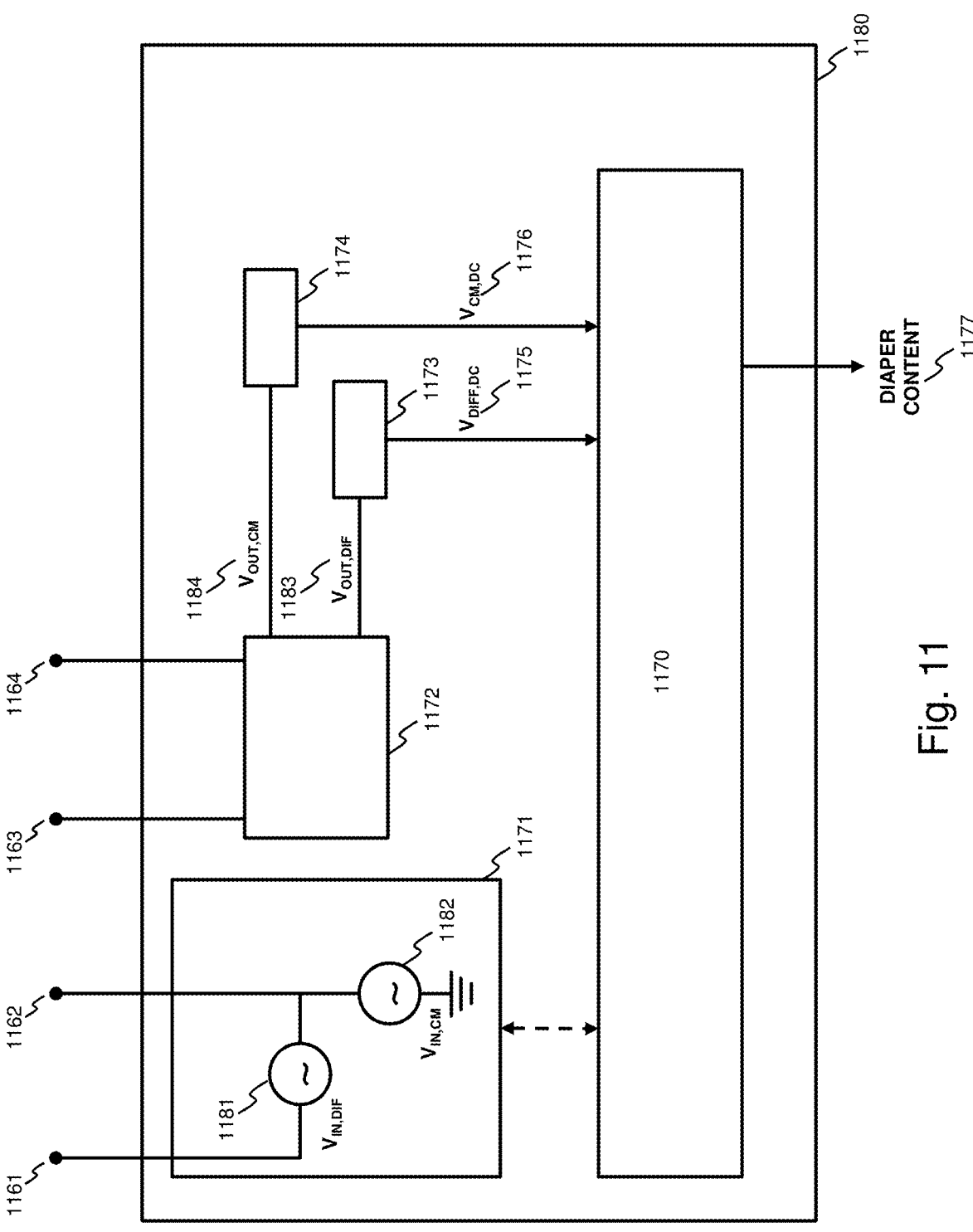
FIG. 11 shows a sensing circuitry according to an example embodiment.

FIG. 11 illustrates a sensing circuitry 1180 for measuring diaper content according to further example embodiment. Circuitry 1180 comprises an excitation circuitry 1171 for generating the differential and common mode excitation signals 1181 and 1182, e.g. signals 181, 182 or 381, 382. Circuitry 1180 further comprises electrical connectors 1161, 1162 for connecting the sensing circuitry 1180 to the input connections of the coupling layer, e.g. to input connections 161, 162 or 361, 362. Sensing circuitry 1180 further comprises a controller 1170 for performing various controlling functions of sensing circuitry 1180. To this end, controller 1170 is arranged to control the performing of excitation circuitry 1171 such as selecting the frequency of the input signals, activating the input signals at certain time intervals and selecting the frequency sweep of the input signals. Sensing circuitry 1180 further comprises electrical connectors 1163, 1164 for receiving differential and common mode output signals in response to the input signals and the inner circuitry layer within the diaper, e.g. signals 183, 184 and 383, 384. To this purpose, connectors 1163 and 1164 are connectable to output connectors 163, 164 and 363, 364 of coupling layer 150, 350. A demultiplexing circuitry 1172 then derives from the measured voltage at connectors 1163 and 1164 the respective differential output signal 1183 and common mode output signal 1184 corresponding to for example signals 183, 184 and 383, 384. Then, an AC to DC conversion is performed on these signals 1183, 1184 by respective circuitries 1173, 1174 that are arranged to output the envelope of the signals 1183, 1184. The resulting differential mode DC signal 1175 is then a measure of the amount of diaper content for a certain amount of coupling. The resulting common mode DC signal 1176 is then a measure of the amount of coupling between the coupling layer and the circuitry within the diaper. These two measurements are then provided to controller 1170 that derives therefrom a quantitative measure 1177 of the diaper content, for example as a percentage of saturation of the diaper's moisture absorbing layer. Controller 1170 may monitor the diaper content continuously or at certain moments in time. Controller 1170 may output the sensed diaper content continuously, at certain moments in time or when the diaper content exceeds a certain threshold. Exceeding such threshold may then indicate that the diaper needs changing.

As used in this application, the term "circuitry" may refer to one or more or all of the following:

(a) hardware-only circuit implementations such as implementations in only analog and/or digital circuitry and (b) combinations of hardware circuits and software, such as (as applicable):

(i) a combination of analog and/or digital hardware circuit(s) with software/firmware and (ii) any portions of hardware processor(s) with software (including digital signal processor(s)), software, and memory(ies) that work together to cause an apparatus, such as a mobile phone or server, to perform various functions) and (c) hardware circuit(s) and/or processor(s), such as microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor (or multiple processors) or portion of a hardware circuit or processor and its (or their) accompanying software and/or firmware. The term circuitry also covers, for example and if applicable to the particular claim element, a baseband integrated circuit or processor integrated circuit for a mobile device or a similar integrated circuit in a server, a cellular network device, or other computing or network device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the scope of the claims are therefore intended to be embraced therein.

It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A system for sensing diaper content comprising:
a diaper comprising an inner circuitry layer having:
inner input capacitor plates;
tracks arranged to provide a resistive coupling between the inner input capacitor plates dependent on the diaper content; and
inner output capacitor plates in galvanic contact with the respective inner input capacitor plates; and
an outer coupling layer having outer input- and output capacitor plates arranged to form respective input- and output capacitors with the inner input- and output capacitor plates in the diaper when the outer coupling layer is provided onto an outside of the diaper; and
a sensing circuitry arranged to:
apply an input signal onto the outer input capacitor plates; and
measure an output signal from the outer output capacitor plates resulting from the input signal and the resistive coupling thereby sensing the diaper content.

2. The system according to claim 1, wherein the tracks and inner input and output capacitor plates are made of printed conductive ink.

3. The system according to claim 2, wherein the conductive ink is a carbon-based conductive ink.

4. The system according to claim 1, wherein the diaper further comprises a moisture absorption layer and a comfort layer; and
wherein the inner circuitry layer is provided between the absorption layer and the comfort layer.

5. The system according to claim 1, wherein the diaper comprises a barrier layer for keeping moisture within the diaper; and wherein the circuitry layer is provided onto the barrier layer.

6. The system according to claim 1, wherein the outer coupling layer is attachable to and removable from the outside of the diaper and is reusable when changing the diaper.

7. The system according to claim 1, wherein the outer coupling layer further comprises conductive tracks arranged to connect the outer capacitor plates with the sensing circuitry.

8. The system according to claim 1, wherein the input signal comprises a differential input signal; and wherein the sensing circuitry is arranged to apply the differential input signal between two outer input capacitor plates, and to measure a differential output signal from two correspondingly connected outer output capacitor plates.

9. The system according to claim 8, wherein the sensing circuitry is arranged to determine a change in the diaper content based on a change in the differential output signal.

10. The system according to claim 9, wherein the input signal comprises a common mode input signal; and wherein the sensing circuitry is arranged to apply the common mode input signal to the two outer input capacitor plates, and to measure a common mode output signal from the two correspondingly connected outer output capacitor plates, and to compensate the measured diaper content for a change in electrical coupling between input and output capacitors based on the common mode output signal.

11. The system according to claim 1, wherein a first inner input capacitor plate of the inner input capacitor plates and a first inner output capacitor plate of the inner output capacitor plates are provided at distal ends of a first track of the tracks and wherein a second inner input capacitor plate of the inner input capacitor plates and a second inner output capacitor plate of the inner output capacitor plates are provided at distal ends of a second track of the tracks thereby defining a detection zone for sensing the diaper content between the first and second track.

12. The system according to claim 11 further comprising a third inner input capacitor plate of the inner input capacitor plates and a third inner output capacitor plate connected to a third track and defining a second detection zone between the third and second track, wherein the first input and output capacitor plate serve as a common node.

13. The system according to claim 1, wherein a first inner input capacitor plate of the inner input capacitor plates and a first inner output capacitor plate of the inner output capacitor plates are provided at a same distal end of a first track of the tracks and wherein a second inner input capacitor plate of the inner input capacitor plates and a second inner output capacitor plate of the inner output capacitor plates are provided at a same distal end of a second track of the tracks thereby defining a detection zone for sensing the diaper content between the first and second track.

* * * * *